United States Patent [19]

Shmueli

[11] Patent Number: 5,704,356
[45] Date of Patent: Jan. 6, 1998

[54] SYSTEM AND METHOD OF DIAGNOSIS OF MALFORMED HIPS IN BABIES OR SMALL ANIMALS

[75] Inventor: Gad Shmueli, Ashkelon, Israel

[73] Assignee: Raycont Ltd., Yafo, Israel

[21] Appl. No.: 643,696

[22] Filed: May 6, 1996

[51] Int. Cl.$^6$ .................................................. A61B 5/05
[52] U.S. Cl. .................... 128/653.1; 128/774; 378/62
[58] Field of Search .................................... 128/774, 898, 128/653.1; 606/97, 53, 86, 201, 130; 602/32; 378/62, 68, 69, 98.3, 207, 98.5, 21

[56] References Cited

U.S. PATENT DOCUMENTS

| | | |
|---|---|---|
| 4,730,212 | 3/1988 | Wojcik et al. |
| 4,774,720 | 9/1988 | Carbon . |
| 4,852,137 | 7/1989 | Mackay . |
| 5,150,394 | 9/1992 | Karellas . |
| 5,187,730 | 2/1993 | Fujihara ................................. 378/97 |
| 5,542,423 | 8/1996 | Bonutti ............................... 128/653.1 |

OTHER PUBLICATIONS

Arvidsson, L., "The Hip Joint: Forces Needed for Distraction and Appearance of the Vacuum Phenonmenon", Scand. J. Rehabil. Med. 22(3) pp. 157–161 (1990) [Abstract].

Cervone de Martino, M. et al., "Neonatal Screening of Congenital Hip Dislocation. Indication of Ultrasonography from a Systematic Study Correlating Clinical Findings and Ultrasonography", Rev. Chir. Orthop. Reparatrice Appar. Mot. 80(4) pp.320–323 (1994) [Abstract].

Larchet, M. et al., "Comparative Evaluation of Clinical and Ultrasonographic Screening of Hip Dislocation in Breton and Languedoc Populations", Arch. Pediatr. 1(12) pp. 1093–1099 (Dec. 1994) [Abstract].

Davids, J.R. et al., "Ultrasonography and Developmental Dysplasia of the Hip: A Cost–Benefit Analysis of Three Delivery Systems", J. Pediatr. Orthop., 15(3) pp. 325–329 (May–Jun. 1995) [Abstract].

Rosendahl, K. et al, "Cost–Effectiveness of Alternative Screening Strategies for Developmental Dysplasia of the Hip", Arch. Pediatr. Adolesc. Med., 149(6) pp. 643–648 (Jun. 1995) [Abstract].

Jomha, N.M. et al, "Ultrasonography in Developmental Hip Dysplasia", J. Pediatr. Orthop., 15 (1), pp. 101–104 (Jan.–Feb. 1995) [Abstract].

Primary Examiner—Marvin M. Lateef
Assistant Examiner—Eleni Mantis Mercader
Attorney, Agent, or Firm—Mark M. Friedman

[57] ABSTRACT

A system and method for diagnosis of dislocated hips in newborn babies. A tensile force is applied to the leg of the subject so as to generate a temporary cavity within the hip in accordance with the vacuum phenomenon. An image is then formed of soft tissue surrounding the cavity. This allows the hip to be identified as either a normal hip or a malformed hip in accordance with the shape of the cavity. The system typically employs two very low dosage X-ray pulses of differing frequencies which are directed through the subject's hip toward a stimulated emission secondary source. The resulting images are sensed using a full-frame CCD, and are combined to form a composite image containing both hard tissue and soft tissue information. The system may also feature a sensor for ensuring that sufficient tensile force is applied to generate a cavity according to the Vacuum Phenomenon.

18 Claims, 3 Drawing Sheets

1

SYSTEM AND METHOD OF DIAGNOSIS OF MALFORMED HIPS IN BABIES OR SMALL ANIMALS

FIELD AND BACKGROUND OF THE INVENTION

The present invention relates to imaging of biological tissue and, in particular, it concerns systems and methods for use in identifying malformed hips in babies or small animals.

It is known that a significant proportion of babies, primarily female, are born with a hip-joint defect known as a congenital displasia of the hip, abbreviated to "CDH". Estimates of the incidence of this condition vary between 1 and 15 per 1000 live births. Identification of this defect within the first few days of life is highly advantageous, allowing immediate and straightforward corrective action which typically results in complete recovery towards normal development of the hip. Delay in treatment, on the other hand, allows contractures of parts of the soft tissue surrounding the hip-joint, resulting in displacement or irreversible malformation of the hip, complicating the treatment and causing progressive hip problems later in life.

Although clinical neonatal procedures include various manipulations intended to detect CDH, these are not sufficiently reliably. It has been suggested to supplement the physical examination by additionally screening using ultrasound imaging techniques. However, ultrasound imaging can only be performed and the results properly evaluated by specially trained personnel, thereby limiting its usefulness for mass screening.

X-ray imaging has been used as a diagnostic tool for many years. Because of the possible harmful effects of high dosages of X-rays, use of X-ray imaging for very young children is conventionally kept to a minimum. Furthermore, conventional X-ray techniques only have diagnostic value after the age of about three months since, until that time, most of the tissue is cartilaginous and is substantially transparent to X-rays.

U.S. Pat. No. 4,852,137 to Mackay, U.S. Pat. No. 5,150,394 to Karellas and U.S. Pat. No. 5,187,730 to Fujihara relate to X-ray-based imaging systems in which the X-rays transmitted through the object of interest fall on a layer of phosphorescent material which acts as a secondary source, converting the pattern of incident X-ray radiation into light. The pattern can then be measured by use of a charge-coupled-device (CCD) to generate an image. This arrangement allows a considerable reduction of intensity of the X-ray radiation used compared to that required for conventional film exposures. The above-referenced U.S. patents are hereby incorporated in their entirety by reference as if fully set out herein.

There is therefore a need for a simple, reliable and cost effective method for screening newborn babies or small animals to identify malformed hips. It would also be advantageous to have a low-dosage X-ray-based system for reliably identifying malformed hips in newborn babies or small animals.

SUMMARY OF THE INVENTION

The present invention is of methods and systems for identifying malformation of a hip in a human or animal subject.

According to the teachings of the present invention there is provided, a method for identifying malformation of a hip in a human or animal subject, the method comprising the steps of: (a) applying tensile force to the leg of the subject so as to generate a temporary cavity within the hip in accordance with the vacuum phenomenon; (b) forming an image of soft tissue surrounding the cavity; and (c) identifying the hip as one of a normal hip and a malformed hip in accordance with the shape of the cavity.

According to a further feature of the present invention, the step of forming an image includes: (a) transmitting X-ray radiation through the soft tissue towards a stimulated emission light source; and (b) sensing light generated by the stimulated emission light source.

According to a further feature of the present invention, the light generated by the stimulated emission light source is sensed by use of a charge-coupled-device having a full-frame shutter.

According to a further feature of the present invention, the X-ray radiation is transmitted for less than about 5 milliseconds.

According to a further feature of the present invention, the X-ray radiation is transmitted for up to about one millisecond.

According to a further feature of the present invention, the X-ray radiation includes a primary pulse of radiation having a first frequency for generating a primary image of soft tissue surrounding the cavity and a secondary pulse of radiation having a second frequency for generating a secondary image of hard tissue surrounding the cavity, the step of forming an image including processing the primary and secondary images to form a composite image.

According to a further feature of the present invention, the step of applying tensile force exerts a corresponding force on a force sensor, the step of forming an image being initiated in response to an output of the force sensor.

There is also provided, according to the teachings of the present invention, a system for use in identification of malformed hips in a human or animal subject, the system comprising: (a) a sensor producing an output indicative of a tensile force applied to the leg of the subject; (b) an X-ray generator responsive to the output to generate at least one pulse of X-ray radiation directed towards the hip of the subject; (c) a phosphorescent screen positioned so as to receive at least part of the X-ray radiation transmitted through the hip, the phosphorescent screen generating light in response to incident X-ray radiation; and (d) a charge-coupled-device for generating an image of the light generated by the phosphorescent screen.

According to a further feature of the present invention, the X-ray generator is activated in response to an output from the sensor indicative of application of a tensile force greater than a threshold value to the leg of the subject.

According to a further feature of the present invention, there is also provided: (a) a weighing platform for generating a measurement of the weight of the subject; and (b) a processor associated with the sensor, the weighing platform and the X-ray generator, the processor being responsive to the measurement of the weight of the subject to calculate the threshold value, the processor then being responsive to an output from the sensor indicative of application of a tensile force greater than the threshold value to activate the X-ray generator.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of methods and systems for identifying malformation of a hip in a human or animal subject.

The principles and operation of systems and methods according to the present invention may be better understood with reference to the drawings and the accompanying description.

By way of introduction, and before addressing the systems and methods of the present invention in detail, a physiological effect known as the "vacuum phenomenon" will be described. It is a particular feature of both the methods and the systems of the present invention that use is made of the vacuum phenomenon to facilitate identification of CDH and other malformations of the hip.

Figure 1A:
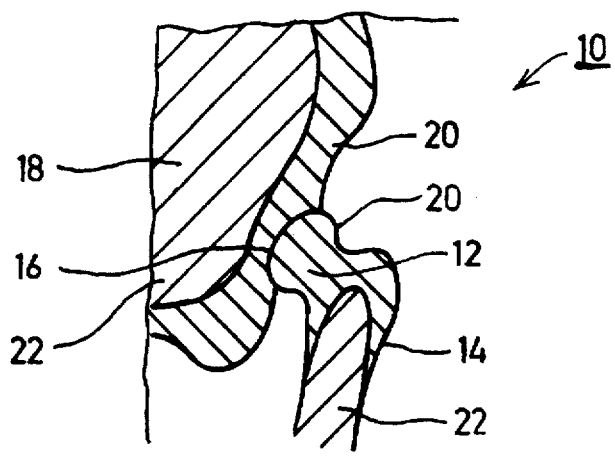
FIG. 1A is a schematic cross-sectional view through the hip joint of a newborn baby.
Figure 1B:
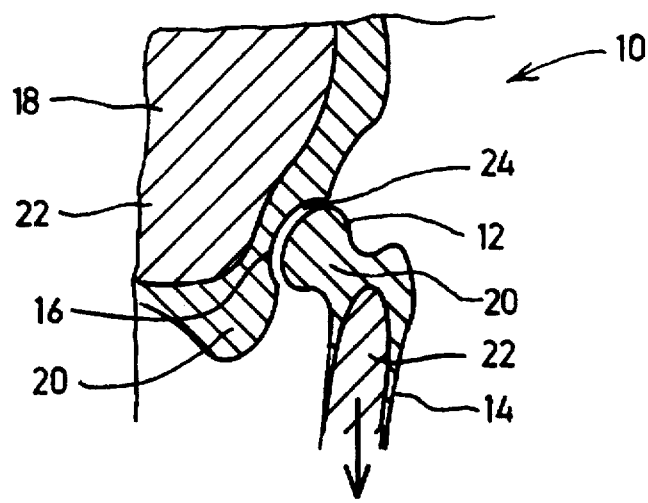
FIG. 1B is a schematic cross-sectional view through the hip joint of FIG. 1A when a longitudinal force is applied to the leg of the baby.
Figure 1C:
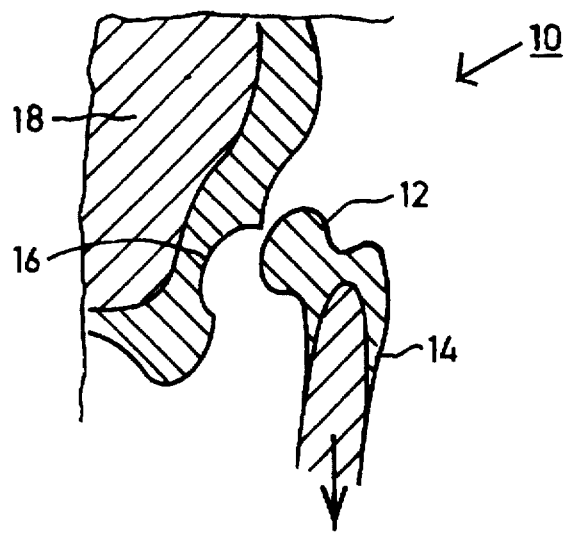
FIG. 1C is a schematic cross-sectional view through a dislocated hip joint of a new baby when a longitudinal force is applied to the leg of the baby.

Referring now to the drawings, FIGS. 1A, 1B and 1C show three different states of a hip joint, generally designated 10, of a newborn baby. For convenience of reference, hip joint 10 will be referred to herein, in the description and claims, as hip 10.

FIG. 1A shows hip 10 as it would appear in a resting position of a normal hip. In this position, the head 12 of the femur 14 is snugly engaged in the socket 16 of the pelvis (acetabulum) 18. Immediately after birth, the portions of both femur 14 and pelvis 18 adjacent to the hip joint are made of cartilage 20 and only the lower part of femur 14 and the inner part of pelvis 18 have hardened to bone 22. Although this fact allows easy correction of a dislocation which is discovered at this stage, the nature of the tissue involved complicates clear imaging of the joint structure by usual X-ray techniques.

FIG. 1B illustrates the effect of applying tensile force to the femur, i.e., the leg, of the healthy hip of FIG. 1A. When sufficient force is exerted, head 12 of femur 14 is temporarily displaced slightly from socket 16, thereby generating a generally crescent-shaped cavity 24 between them. This effect is known as the "Vacuum Phenomenon". The cavity has the same radio-translucency as air and appears as a black shape on usual X-ray images.

FIG. 1C illustrates the effect of applying a tensile force similar to that applied in FIG. 1B to a dislocated hip. In this case, head 12 of femur 14 is not firmly bound to socket 16, so that any gap formed between femur 14 and pelvis 18 is irregular in shape.

Figure 2:
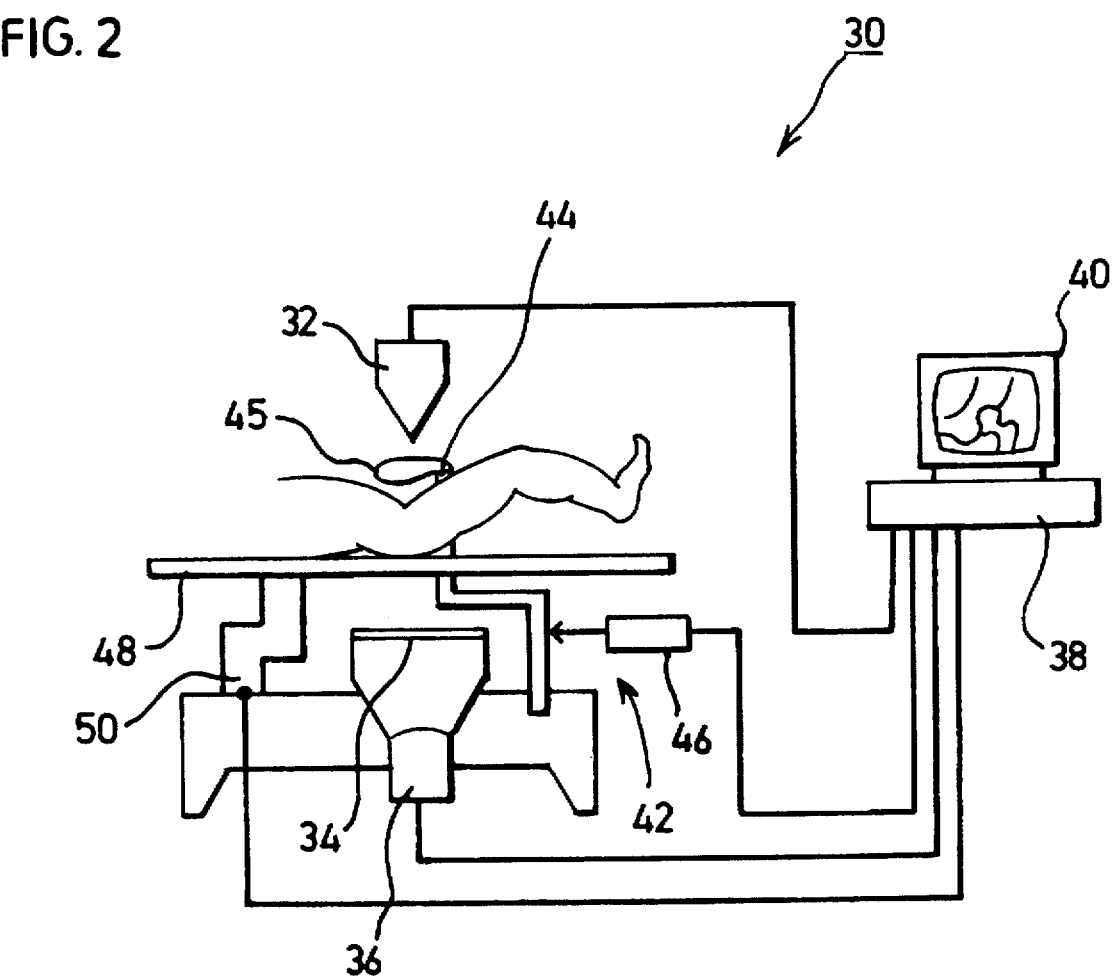
FIG. 2 is a schematic side view of a system, constructed and operative according to the teachings of the present invention, for identifying malformed hips in newborn babies or small animals.

Turning now to FIG. 2, there is shown a system, generally designated 30, constructed and operative according to the teachings of the present invention, for identifying malformed hips in newborn babies or small animals. The system may also be used for analysis of the condition of a malformed hip during or after treatment. Although system 30 may be used effectively on a range of nonhuman subjects of various types, it will be illustrated herein, by way of example only, in relation to human babies.

Generally speaking, system 30 includes an X-ray generator 32 for generating a pulse of X-ray radiation directed towards the hip of the baby, a phosphorescent screen 34 positioned so as to receive at least part of the X-ray radiation transmitted through the hip, for generating light in response to the incident X-ray radiation, and a charge-coupled-device (CCD) 36 for generating an image of the light generated by phosphorescent screen 34. System 30 is then employed to form an image of soft tissue of the hip while a sufficient tensile force is applied to the leg of the baby to generate a cavity within the hip in accordance with the vacuum phenomenon. The hip is then identified as either normal or malformed on the basis of the shape of the cavity observed.

It will be appreciated from the following description that system 30 represents a low-cost and simple-to-use system requiring only a brief training for the operator and suited for widespread use in a program of mass screening for CDH.

Turning now to the features of system 30 in more detail, it is a particular feature of the present invention that X-ray generator 32 delivers one or more short pulses of very low intensity radiation. Typically, X-ray generator 32 is designed to transmit a pulse of less than about 5 milliseconds, and preferably, up to about one millisecond, at an energy of less than about 75 kV. Preferably, a dual frequency X-ray source is used to provide a primary pulse for generating an image of soft tissue so as to differentiate between fat, muscle and cartilage in the region of the hip surrounding the cavity, and a secondary pulse at a second frequency for generating a secondary image of hard tissue such as bone. Typically, the primary pulse employs X-rays in the energy range of about 25–30 kV, and the secondary pulse employs X-rays of about 70 kV. Although labelled "primary" and "secondary", the two X-ray pulses may be performed in either order. The time delay between them is generally a small fraction of a second, but must be significantly longer than the memory of phosphorescent screen 34.

Phosphorescent screen 34 is preferably made using rare-earth phosphor which is highly sensitive and has a "memory" of a few thousandths of a second. Alternatively, any other stimulated emission light source which generates visible or invisible light may be used. It should be understood in this context that the term "phosphorescent" is used to refer to the properties of the material as a stimulated emission light source, and is not intended to imply specifically a phosphor-containing material.

CCD 36 is preferably a full-frame shutter device. By avoiding any scanning process during generation of the image, it is possible to form an image from a single short pulse of x-ray radiation. This allows the dosage of X-ray pulses employed by the present invention to be very much smaller than that of conventional X-ray imaging techniques, thereby making system 30 acceptable for use with babies.

For example, a typical conventional system for use in dental applications or the like employs a 20 millisecond pulse of 100 mA corresponding to a dosage of 2 mA s. In contrast, the device of the present invention delivers two pulses each of up to about 1 millisecond, typically of about 50 mA. This corresponds to a dosage of less than 0.1 mA s, or less than 5% of the conventional dosage.

System 30 also features a processor 38. Processor 38 serves to synchronize the operation of X-ray generator 32 and CCD 36, and to process the output of CCD 36 to generate the desired image. The image is then typically displayed on a display screen 40 to enable immediate diagnosis. Alternatively, or additionally, the image may be transferred to a local computer or remote network, such as for automated analysis or for storage within a database.

In the case that a single pulse X-ray exposure is employed, processor 38 performs only trivial image processing. In a preferred embodiment, two exposures of different frequencies are employed to provide information about both soft tissues (fat, muscle and cartilage) and hard tissue in the region of the baby's hip. In this case, processor 38 performs algorithms for combining the two electronic images to form a single composite image. Such algorithms are generally known in other areas of medical imaging, as well as in the fields of aerial imaging and astronomical research, and will therefore not be described here in detail.

It is a further feature of a preferred embodiment of the present invention that system 30 is activated only when sufficient tensile force is applied to the leg of the baby to generate the Vacuum Phenomenon. In order to ensure that the necessary force is being applied, a force sensor 42 is provided which produces an output indicative of a tensile force applied to the leg of the baby. Force sensor 42 typically includes a lever 44 pivotally attached at one end and extending between the legs of the baby, and a pneumatic pressure gauge 46 acted upon by lever 44. An electrical output from pneumatic pressure gauge 46 is supplied to processor 38. Processor 38 is programmed to disable activation of system 30 unless pneumatic pressure gauge 46 indicates that the tensile force currently being applied to the leg of the baby is above some threshold value considered sufficient to generate a cavity in accordance with the Vacuum Phenomenon. System 30 may be programmed to be activated either directly in response to above-threshold tensile force, or manually contingent on the presence of above-threshold tensile force. It should be noted that, while the present invention has been described in an embodiment in which the force applied the leg of the baby is longitudinal, comparable results may be achieved by applying tensile force in other directions. In a case in which a different direction of force is to be used, the structure of force sensor 42 may be varied accordingly.

In a preferred feature of the present invention, an X-ray shield made from lead or other X-ray absorbent material is provided to protect the genital region of the baby from potentially damaging X-ray radiation. This shield may conveniently be formed as a butterfly-shaped device 45 attached to the upper end of lever 44.

For convenience of use, the components of system 30 are, in general, mounted in relation to a traction table 48 on which the baby is placed during the imaging process. In this case, lever 44 extends through a slot (not shown) through traction table 48. Traction table 48 is either made from a substantially X-ray-transparent material, or has an opening corresponding to the operative imaging area of the table.

It has been found that the force necessary to generate a cavity according to the Vacuum Phenomenon is directly correlated to the weight of the baby. In order to estimate correctly the appropriate force threshold to be used for each baby, it is therefore preferable to supply processor 38 with a measurement of the weight of the baby. For this purpose, the traction table 48 on which the baby is placed is preferably mounted on a load cell 50 or other weighing mechanism thereby forming a weighing platform which supplies a weight measurement to processor 38. Alternatively, a conventional free-standing electronic scale may be used as a weighing platform to weigh the baby prior to imaging. The weight measurement is then supplied electronically or manually to processor 38.

In use, the baby is first placed on the weighing platform and its weight input to processor 38. Processor 38 then calculates the appropriate force threshold value necessary to generate the Vacuum Phenomenon for this baby. The baby is then held in position with lever 44 between its legs with one hip aligned between X-ray generator 32 and phosphorescent screen 34. Traction is then applied to the baby's leg, typically by hand, and, when processor 38 determines that sufficient tensile force is being applied, X-ray generator 32 is activated. The simplicity of the system and its operation enables it to be operated by semi-skilled personnel with relatively brief training.

X-ray generator 32 transmits a primary and a secondary pulse, as detailed above, typically about a twentieth of a second apart. Each pulse generates an image on phosphorescent screen 34 which is sensed by CCD 36 and input into processor 38. Processor 38 then processes the images to form a single compound image which is then displayed on display screen 40, and may also be stored electronically or printed for inclusion in medical records.

Figure 3A:
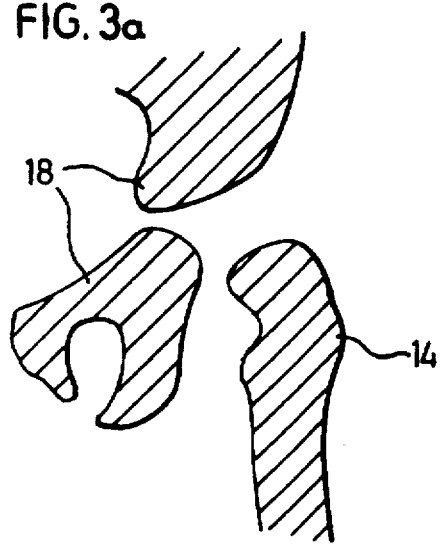
FIG. 3A is a schematic representation of an X-ray image of a hip joint taken without inducing the vacuum phenomenon.

FIGS. 3A to 3D illustrate the X-ray images which would be expected under various different conditions. FIG. 3A illustrates the difficulty of accurate diagnosis in the absence of a vacuum phenomenon cavity. Since all the soft tissue is usually indistinguishable, the structure of the hip joint is unclear.

Figure 3B:
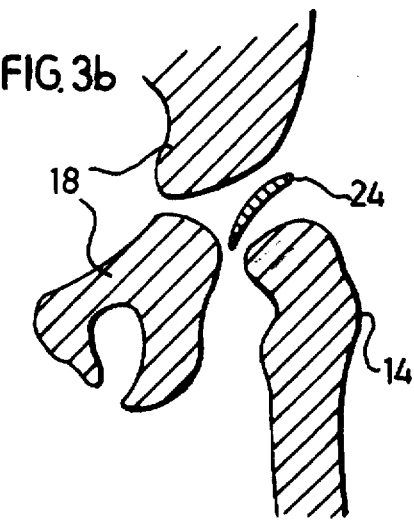
FIG. 3B is a view similar to FIG. 3A showing the shape of a cavity formed by the vacuum phenomenon in a normal hip.

In contrast, FIG. 3B shows the image of a normal hip subjected to sufficient force to generate a cavity in accordance with the vacuum phenomenon. In this case, a distinct crescent-shaped cavity allows rapid identification of the hip as normal.

Figure 3C:
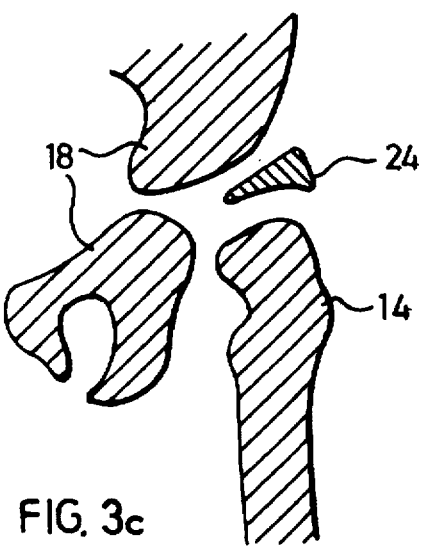
FIG. 3C is a view similar to FIG. 3A showing the shape of a cavity formed by the vacuum phenomenon in a hip exhibiting congenital displasia of the hip (CDH)

FIG. 3C shows an image comparable to that of FIG. 3B, but with an irregularly shaped cavity. This irregularity is indicative of a malformation such as CDH.

Figure 3D:
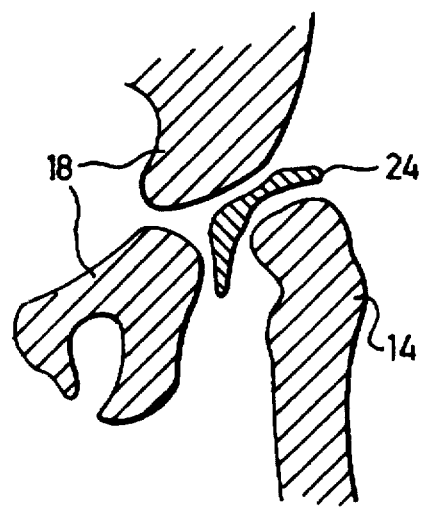
FIG. 3D is a view similar to FIG. 3A showing the shape of a cavity formed by the vacuum phenomenon in a dislocated hip.

Finally, FIG. 3D shows the more extended irregular shape of the cavity in a case of hip displacement.

It will be appreciated that the above descriptions are intended only to serve as examples, and that many other embodiments are possible within the spirit and the scope of the present invention.

What is claimed is:

1. A method for identifying malformation of a hip in a human or animal subject, the method comprising the steps of:
   (a) applying tensile force to the leg of the subject so as to generate a temporary cavity within the hip in accordance with the vacuum phenomenon;
   (b) forming an image of soft tissue surrounding said cavity; and
   (c) identifying the hip as one of a normal hip and a malformed hip in accordance with the shape of said cavity, wherein said step of applying tensile force exerts a corresponding force on a force sensor, said step of forming an image being initiated in response to an output of said force sensor.

2. The method of claim 1, wherein said step of forming an image includes:

(a) transmitting X-ray radiation through said soft tissue towards a stimulated emission light source; and (b) sensing light generated by said stimulated emission light source.

3. The method of claim 2, wherein said light generated by said stimulated emission light source is sensed by use of a charge-coupled-device having a full-frame shutter.

4. The method of claim 2, wherein said X-ray radiation is transmitted for less than about 5 milliseconds.

5. The method of claim 2, wherein said X-ray radiation is transmitted for up to about one millisecond.

6. The method of claim 2, wherein said X-ray radiation includes a primary pulse of radiation having a first frequency for generating a primary image of soft tissue surrounding said cavity and a secondary pulse of radiation having a second frequency for generating a secondary image of hard tissue surrounding said cavity, said step of forming an image including processing said primary and secondary images to form a composite image.

7. A system for use in identification of malformed hips in a human or animal subject, the system comprising:

(a) a sensor producing an output indicative of a tensile force applied to the leg of the subject;

(b) an X-ray generator responsive to said output so as to generate at least one pulse of X-ray radiation directed towards the hip of the subject when said output from said sensor is indicative of application of a tensile force greater than a threshold value to the leg of the subject;

(c) a phosphorescent screen positioned so as to receive at least part of said X-ray radiation transmitted through the hip, said phosphorescent screen generating light in response to incident X-ray radiation; and (d) a charge-coupled-device for generating an image of said light generated by said phosphorescent screen.

8. The system of claim 7, further comprising:

(a) a weighing platform for generating a measurement of the weight of the subject; and (b) a processor associated with said sensor, said weighing platform and said X-ray generator, said processor being responsive to said measurement of the weight of the subject to calculate said threshold value, said processor then being responsive to an output from said sensor indicative of application of a tensile force greater than said threshold value to activate said X-ray generator.

9. A method for identifying malformation of a hip in a human or animal subject, the method comprising the steps of:

(a) applying tensile force to the leg of the subject so as to generate a temporary cavity within the hip in accordance with the vacuum phenomenon;

(b) forming an image of soft tissue surrounding said cavity including:

(i) transmitting X-ray radiation for less than about 5 milliseconds through said soft tissue towards a stimulated emission light source, and (ii) sensing light generated by said stimulated emission light source; and (c) identifying the hip as one of a normal hip and a malformed hip in accordance with the shape of said cavity.

10. The method of claim 9, wherein said X-ray radiation is transmitted for up to about one millisecond.

11. The method of claim 9, wherein said light generated by said stimulated emission light source is sensed by use of a charge-coupled-device having a full-frame shutter.

12. The method of claim 9, wherein said X-ray radiation includes a primary pulse of radiation having a first frequency for generating a primary image of soft tissue surrounding said cavity and a secondary pulse of radiation having a second frequency for generating a secondary image of hard tissue surrounding said cavity, said step of forming an image including processing said primary and secondary images to form a composite image.

13. The method of claim 9, wherein said step of applying tensile force exerts a corresponding force on a force sensor, said step of forming an image being initiated in response to an output of said force sensor.

14. A method for identifying malformation of a hip in a human or animal subject, the method comprising the steps of:

(a) applying tensile force to the leg of the subject so as to generate a temporary cavity within the hip in accordance with the vacuum phenomenon;

(b) forming an image of soft tissue surrounding said cavity including:

(i) transmitting X-ray radiation through said soft tissue towards a stimulated emission light source, said X-ray radiation including a primary pulse of radiation having a first frequency for generating a primary image of soft tissue surrounding said cavity and a secondary pulse of radiation having a second frequency for generating a secondary image of hard tissue surrounding said cavity, (ii) sensing light generated by said stimulated emission light Source, and (iii) processing said primary and secondary images to form a composite image; and (c) identifying the hip as one of a normal hip and a malformed hip in accordance with the shape of said cavity.

15. The method of claim 14, wherein said light generated by said stimulated emission light source is sensed by use of a charge-coupled-device having a full-frame shutter.

16. The method of claim 14, wherein said X-ray radiation is transmitted for less than about 5 milliseconds.

17. The method of claim 14, wherein said X-ray radiation is transmitted for up to about one millisecond.

18. The method of claim 14, wherein said step of applying tensile force exerts a corresponding force on a force sensor, said step of forming an image being initiated in response to an output of said force sensor.

* * * * *